United States Patent
Sullivan et al.

(10) Patent No.: US 9,968,632 B2
(45) Date of Patent: *May 15, 2018

(54) FAST ACTING JOINT RELIEF FORMULATIONS

(71) Applicants: James Sullivan, Plantation, FL (US); Forrest Haag, Wilton Manors, FL (US); Lianne Maso de Moya, Coral Springs, FL (US)

(72) Inventors: James Sullivan, Plantation, FL (US); Forrest Haag, Wilton Manors, FL (US); Lianne Maso de Moya, Coral Springs, FL (US)

(73) Assignee: Natures Products, Inc., Sunrise, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/805,079

(22) Filed: Nov. 6, 2017

(65) Prior Publication Data

US 2018/0055874 A1    Mar. 1, 2018

Related U.S. Application Data

(63) Continuation of application No. 15/345,399, filed on Nov. 7, 2016, now Pat. No. 9,808,483, which is a continuation of application No. 14/819,385, filed on Aug. 5, 2015, now Pat. No. 9,486,476.

(60) Provisional application No. 62/033,416, filed on Aug. 5, 2014, provisional application No. 62/033,565, filed on Aug. 5, 2014.

(51) Int. Cl.

| | | |
|---|---|---|
| A61K 36/00 | (2006.01) |
| A61K 31/737 | (2006.01) |
| A61K 31/56 | (2006.01) |
| A61K 35/618 | (2015.01) |
| A61K 31/232 | (2006.01) |
| A61K 36/76 | (2006.01) |
| A61K 36/232 | (2006.01) |
| A61K 36/324 | (2006.01) |
| A61K 9/48 | (2006.01) |
| A61K 9/00 | (2006.01) |
| A61K 31/7034 | (2006.01) |
| A61K 31/19 | (2006.01) |
| A61K 31/7008 | (2006.01) |
| A61K 31/202 | (2006.01) |

(52) U.S. Cl.
CPC ......... *A61K 31/737* (2013.01); *A61K 9/0053* (2013.01); *A61K 9/4825* (2013.01); *A61K 9/4858* (2013.01); *A61K 9/4875* (2013.01); *A61K 31/19* (2013.01); *A61K 31/202* (2013.01); *A61K 31/232* (2013.01); *A61K 31/56* (2013.01); *A61K 31/7008* (2013.01); *A61K 31/7034* (2013.01); *A61K 35/618* (2013.01); *A61K 36/232* (2013.01); *A61K 36/324* (2013.01); *A61K 36/76* (2013.01); *A61K 2300/00* (2013.01)

(58) Field of Classification Search
CPC ..................................................... A61K 36/00
USPC .......................................................... 424/725
See application file for complete search history.

(56) References Cited

U.S. PATENT DOCUMENTS 8,222,295 B2 *  7/2012  Fortin .................. A61K 31/232
                                                          424/195.17

* cited by examiner

*Primary Examiner* — Michael V Meller

(57) ABSTRACT

The instant invention provides a method and composition for treating or preventing osteoarthritis, joint effusion, joint inflammation and pain, synovitis, lameness, post operative arthroscopic surgery, deterioration of proper joint function including joint mobility, the reduction or inhibition of metabolic activity of chondrocytes, the activity of enzymes that degrade cartilage, said method comprising administering effective amounts of *Boswellia Serrata*, effective amounts of freeze dried green lipped mussle, effective amounts of white willow bark extract containing salicin, effective amounts of *angelica* root, effective amounts of glucosamine and salts thereof, effective amounts of chondroitin and salts thereof and effective amounts of omega 3 fatty acids.

1 Claim, No Drawings

FAST ACTING JOINT RELIEF FORMULATIONS

This application is a continuation of U.S. application Ser. No. 15/345,399 filed on Nov. 7, 2016 now U.S. Pat. No. 9,808,483 issued Nov. 7, 2017; which application is a continuation of U.S. application Ser. No. 14/819,385 filed Aug. 5, 2015; now U.S. Pat. No. 9,486,476 issued Nov. 8, 2016; the entired contents of which are incorporated by reference herein. This application also claims the priority benefit under 35 U.S.C. section 119 of U.S. Provisional Patent Application Nos. 62/033,416 entitled "Fast Acting Joint Relief Formulations" filed on Aug. 5, 2014; and 62/033,565 entitled "Fast Acting Joint Relief Formulations" filed Aug. 5, 2014, which are in their entirety herein incorporated by reference.

FIELD OF INVENTION

This invention relates to methods and compositions for the prevention and treatment of osteoarthritis in a mammal. More particularly, the present invention relates to compositions and methods for reducing inflammation and pain associated with acute inflammation of body parts, particularly joints, due to injury or due to arthritic conditions or other disease conditions.

The present invention relates generally to compositions and methods for treating joints. This invention also relates to a mixture of natural ingredients for the treatment of bone or joint inflammation. The instant invention is also generally related to chemical formulations and methods for administration of a natural chemical formulation to mammals and, more particularly, is related to natural chemical formulations directed towards reducing muscle and joint soreness and methods of administration thereof. The present invention also relates to pharmaceutical preparations for the treatment of degenerative afflictions of the joints.

The present invention is generally further directed to compositions useful for the treatment and/or prevention of damage to diarthrodial (synovial) joints and, in particular traumatic synovitis, inflammation of the synovial membrane, and damage to the articular cartilage of the joint. Specifically, the invention relates to compositions specially formulated for oral administration in the treatment and/or prevention of traumatic synovitis and damage to articular cartilage, e.g., for post surgical joint lavage or treatment and/or prevention of inflammatory arthritis, osteoarthritis (OA) and/or degenerative joint disease (DJD).

The instant invention also relates generally to the treatment of cartilage disorders, including stimulation of cartilage repair and treatment of degenerative cartilagenous disorders. The present invention also concerns compositions and methods of treating arthritis, repairing of articular joint surfaces and relief of symptoms associated with arthritis.

This invention also relates to compositions having natural components. More particularly, this invention relates to a natural composition capable of reducing inflammation in bones and joints. The present invention further relates to methods of using such natural compositions to reduce inflammation.

The instant invention also relates to a method for treating diseases characterized by connective tissue destruction and, more specifically, to a method for treating articular diseases, characterized by destruction of collagen which is a major constituent of connective tissues. The present invention further relates to therapeutic compositions for the repair of connective tissue in mammals and, in particular to "nutraceutical" compositions capable of promoting chondroprotection, the repair and replacement of mammalian connective tissue.

The present invention is also directed to formulations, and methods using such formulations, that when administered to an animal, arrest the inflammatory response in affected tissues and facilitate repair and maintenance of damaged tissues in the joints of vertebrates.

Considering the complexity of symptoms related to different kinds of arthritis and inflammatory disease, there is still a need for compositions which include analgesic and anti-inflammatory components, as well as components to protect against the abrasion of connective tissue and to support its production. Considering different side effects of current treatments, also a need for compositions remains to avoid side effects like dyspepsia, ulcer and gastrointestinal bleeding and designed for both, short-term and long-term treatment.

BACKGROUND OF THE INVENTION

In healthy conditions, articular cartilage forms a smooth surface between articulating bone ends to reduce the friction caused by movement. This friction is further reduced by the synovial fluid. Articular cartilage consists of chondrocytes and two major macro-molecules; i.e., collagen and proteoglycans, which are synthesized by and deposited around the chondrocytes. The chondrocytes also synthesize the synovial fluid which bathes the articular cartilage.

The structural integrity of the articular cartilage is the foundation of optimal functioning of the skeletal joints in the hip, shoulders, elbows, hocks and stifles. Impaired function of skeletal joints will dramatically reduce mobility such as rising from sitting position or climbing and descending stairs. To maintain the structural integrity and the proper functioning of the articular cartilage, the chondrocytes constantly synthesize collagen and proteoglycans, the major components of the articular cartilage, as well as the friction-reducing synovial fluid. This constant synthesis of the macro-molecules and synovial fluid provides the articular cartilage with the repairing mechanism for most of the wearing caused by friction between the bone ends. However, it also leads to the constant demand for the supply of precursors, or building blocks, for the macromolecules and synovial fluid. Lack of this precursors will lead to defects in the structure and function of the skeletal joints. This deficiency occurs often when activity levels are very high, or cartilage tissue has been traumatized.

Degradation of the structures in articular cartilage is a typical characteristic of all diseases resulting in chronic destruction of the joint structures. Examples of such disorders are rheumatoid arthritis, psoriatic arthritis, and osteoarthrosis. Also, acute inflammation of a joint is often accompanied by destruction of the cartilage, although in most cases this will not develop into the chronically destructive disease. It is not known which factors are crucial for the acutely inflamed joint to either proceed to healing or develop into the chronic process. Examples of to diseases involving acute joint inflammation are *yersinia* arthritis, pyrophosphate arthritis, gout arthritis (arthritis urica), septic arthritis and various forms of arthritis of traumatic etiology. Among other factors potentially conducive to the destruction of articular cartilage may be mentioned, for instance, treatment with cortisone; this has been known for a long time to accelerate the degenerative process in osteoarthrosis.

An adequate supply of metabolic precursors or building blocks is thus paramount to replacement and repair of the constituents of skeletal joints, connective tissue and synovial fluid. Proteoglycans (or mucopolysaccharides) form the ground substance of cartilage, bone and joint fluid. Proteoglycans are comprised of proteins linked to glycosaminoglycans (GAGS). The building block GAG subunit of the proteoglycan in cartilage and bone is chondroitin sulfate. Chondroitin sulfate A is present in cornea and cartilage. Chondroitin sulfate B (G-heparin) is found in tendon, aorta, skin and heart valves. Chondroitin C is found in cartilage, tendon and umbilical cord and similar tissues. The building block GAG subunit of the proteoglycan in joint fluid is hyaluronic acid. Intercellular solutions of hyaluronic acid are viscous and thus assist in lubrication of the joints of body skeleton. Hyaluronic acid is synthesized from the metabolic precursor, glucosamine. The availability of glucosamine in cartilage tissue can be rate-limiting to the enzymatic step leading to the production of proteoglycans. Exogenous glucosamine serves to drive the biosynthetic pathway forward past the rate-limiting blockage point. Glucosamine serves as a substrate for a kinase enzyme which yields glucosamine-6-phosphate, the rate-limiting precursor in proteoglycan synthesis.

Recently, studies have reported the suppression of autoimmune disorders such as rheumatoid arthritis upon ingestion of cartilage fibers derived from chickens and sharks. The therapy, termed oral tolerization, is not fully understood but it is theorized that a mechanism in the digestive tract disarms immune cells that would otherwise assault food molecules as foreign intruders to the body, akin to foreign substances that enter the blood stream by means other than the gastrointestinal tract. Apparently, the immune-disarming effect occurs not only in the gut, but also in the vulnerable tissues.

Also, it is well known that articular cartilage is composed of about 70% of water, chondrocytes and a cartilage matrix. The major components constituting the articular matrix are collagen and proteoglycan; the proteoglycan having good water retention characteristics is contained in the network of collagen having a reticulated structure. The articular matrix is rich in viscoelasticity and has an important role in reducing the stimulus and load imposed on the cartilage in order to maintain the normal morphology and function of the articular cartilage.

Osteoarthritis and rheumatoid arthritis are representative of the diseases accompanied by the destruction of the cartilage matrix. It is thought that the destruction of the matrix in these diseases is triggered by mechanical stresses with aging in the case of osteoarthritis and by excess proliferation of the surface layer cells of the synovial membrane, pannus formation and inflammatory cell infiltration in the case of rheumatoid arthritis, and both phenomena are caused through the induction of proteases. Since the degradation of articular cartilage is progressed in the extracellular region at a neutral pH, it is said that a matrix metalloprotease (hereinafter referred to as "MMP" or "MMPs" when used as the general term) whose optimal pH is in the neutral range plays a leading role in the degradation.

Numerous disclosures describe therapy of damaged tissues by introduction of precursors in the metabolic pathway leading to biosynthesis of the macromolecules of connective tissues. For example, in U.S. Pat. No. 3,697,652 (Rovati et al.), N-acetylglucosamine is used to treat degenerative afflictions of the joints. In U.S. Pat. No. 3,683,076 (Rovati et al.), glucosamine salts are described as pharmaceutically useful for treatment of osteoarthritis and rheumatoid arthritis. U.S. Pat. No. 4,647,453 (Meisner) and U.S. Pat. No. 4,772,591 (Meisner) disclose the use of glucosamine salts for treatment of degenerative inflammatory disease and as a means of accelerating wound healing. In U.S. Pat. No. 4,801,619 (Lindblad), a hyaluronic acid preparation is claimed to be effective for treatment of steroid arthropathy and progressive cartilage degeneration caused by proteoglycan degradation. A combination of glucosamine, chondroitin and manganese is claimed in U.S. Pat. No. 5,364,845 (Henderson) as a means of protecting and repair of connective tissue. None of these prior investigators, however, disclose a composition having metabolic precursors, herbal phytochemicals and palatability agents that work synergistically to prevent and treat joint and connective tissue disorders.

No medical cure exists for osteoarthritis. The progressive degeneration of the joint due to osteoarthritis is irreversible. Present therapies are directed to palliative medical therapies to reduce inflammation and pain and surgical therapies to reconstruct an affected joint or, in severe cases, to replace the joint with an artificial, prosthetic joint.

A need exists for an effective palliative medication for the treatment of osteoarthritis and other joint diseases which is both safe and effective when used for both short-term and long-term therapy and which can be administered orally.

SUMMARY OF THE INVENTION

The invention provides a composition for the treatment of arthritis, joint stiffness, joint mobility and joint pain in vertebrates, comprising: effective amounts of a source of boswellic acid and effective amounts of *Angelica* root extract.

The present invention relates to prophylaxis and therapy of joint disorders in vertebrates accomplished by oral administration of a combination of natural physiological compounds and herbal phytochemicals. Arthritic disorders, including rheumatism, osteoarthritis, dysplasia, lupus, bursitis and gout, are all characterized by inflammation and pain in joints, muscles and related connective tissues. Most of the forms are progressive. The present inventors disclose for the first time herein a beneficial effect of the natural physiological compounds and herbal phytochemicals for treatment of joint disorders in vertebrates.

The present invention is directed to a composition capable of eliminating or diminishing inflammation and in accelerating the tissue repair process. Even though prior investigators used anti-inflammatory substances, their compositions did not provide a complete array of necessary repair and maintenance precursor building blocks along with anti-inflammatory substances. Furthermore, the anti-inflammatory substances utilized by prior investigators are not comprised of natural herbal phytochemicals. In fact, it is known that some substances which exhibit anti-inflammatory responses, such as glucosamine, do not exert general activity. Instead, the response may be mediator specific. Thus, one aspect of the present invention relates to the provision of multiple anti-inflammatory herbal phytochemicals that have more general reactivity and, hence, are more efficacious in a broader population.

The present invention provides a method for treating or preventing osteoarthritis, joint effusion, joint inflammation and pain, synovitis, lameness, post operative arthroscopic surgery, deterioration of proper joint function, the reduction or inhibition of metabolic activity of chondrocytes, the activity of enzymes that degrade cartilage, the reduction or inhibition of the production of hyaluronic acid, said method comprising orally administering to a mammalian species a therapeutically effective amount of natural physiological compounds and herbal phytochemicals.

The invention is also directed to a Chondroprotective/Restorative composition comprising natural physiological compounds and herbal phytochemicals and optionally a pharmaceutically acceptable carrier.

DETAILED DESCRIPTION OF INVENTION

The invention provides a composition comprising effective amounts of *Boswellia Serrata*, effective amounts of freeze dried green lipped mussle, effective amounts of white willow bark extract containing salicin, effective amounts of glucosamine and salts thereof, effective amounts of chondroitin and salts thereof and effective amounts of omega 3 fatty acids.

The invention also provides a composition comprising effective amounts of *Boswellia Serrata*, effective amounts of freeze dried green lipped mussle, effective amounts of white willow bark extract containing salicin, effective amounts of glucosamine and salts thereof, effective amounts of *angelica* root extracts and effective amounts of omega 3 fatty acids.

The invention further provides a composition containing 100-1000 mgs of *Boswellia serrata*, 250-1000 mgs of freeze dried green lipped mussel, 35-500 mgs of white willow bark containing 15% by weight salicin, 100-450 mgs of glucosamine sulfate potassium, 5-20 mgs of *angelica* root extracts 4:1, 10-40 mgs of omega 3 fatty acids and inert pharmaceutical excipients.

Without wishing to be limiting, the *Boswellia* gum, gel, resin or extract or dried extract may be derived from the leaves, plant or roots of *Boswellia serrata* or other species of *Boswellia*, such as *Boswellia sacra* or *Boswellia carterii*. In a preferred embodiment, the composition comprises about 10% to 99% boswellic acids (e.g. as measured by UV-VIS spectrometry analysis, HPLC diode array or the like).

In an embodiment, the *Boswellia* gum, gel, resin or extract or dried extract is derived from the leaves, plant or roots of *Boswellia serrata*, or other species of *Boswellia* such as *Boswellia sacra*, *Boswellia carterii*, and contains between about 10% and 99% boswellic acids, for example but not limited to about 10%, 20%, 30%, 40%, 50%, 60%, 70%, 80%, 90%, 99% or any value therein between. The amount of boswellic acids may also be defined by a range of any two of the values listed above or any value therein between, and can be measured, for instance, by UV-VIS spectrometry analysis, HPLC diode array or other non-limiting method. More preferably the *Boswellia* gum, gel, resin or extract contains between about 50% to 79% boswellic acids.

By way of non-limiting example, *boswellia serrata* is a source of boswellic acid, which may provide relief from pain and inflammation. Other sources of boswellic acid may include for example, extracts of: *Boswellia bhau-dajiana*, *Boswellia frereana*, *Boswellia papyrifera*, Sudanese *Boswellia sacra*, and *Boswellia carterii*, *Commiphora incisa*, *Commiphora myrrha*, *Commiphora abyssinica*, *Commiphora erthraea*, *Commiphora molmol*, and *Bursera microphylla*, may be used as a substitute for or in conjunction with *boswellia serrata*.

The preferred mussel extract used in the present invention is an extract or freeze dried powder of the New-Zealand green-lipped mussel (*Perna canaliculus*) and contains substances having a beneficial anti-inflammatory effect. The preparation of the Mussel extract is described in the New Zealand patent application No. 328489, which relates to an anti-inflammatory composition including a freeze-dried substance containing proteins. The product containing the substance extracted from green-lipped mussel possesses chondroprotective, gastro protective and anti-inflammatory activity and is beneficial to sufferers of many of the arthritic disorders. A typical composition is a green-lipped mussel extract containing by weight 0.65-3.21% of moisture, 0.67-10.54% of lipids, 52.13-55.6% of carbohydrates and 11.7-14.9% of ash. This is a very suitable extract for the present invention. A suitable green lipped mussel powder is sold as Biolane in the market place.

The willow bark or *salicis* cortex of the invention consists of the bark of the young, 2-3-year-old branches harvested during early spring of *Salix alba* L, *S. purp[upsilon]res* L, *S. fragilis* L. and other comparable *Salix* species (Salicaceae), as well as their preparations in effective dosage. The bark contains at least 2 percent total salicin derivates, calculated as salicin and related to dried herb. Antipyretic, analgesic and antiphlogistic effects are described for the willow bark. Administration of Willow Bark leads to positive effects in non-human animals suffering from arthritis. Positive effects are recognized in the symptoms that accompany this disease, i.e. fever, rheumatic ailments and headaches. For Willow Bark the same is true as for the other substances characterized herein, namely that much better results are obtained after the administration of a combination of products rather than by applying only one component. A preferred willow bark component contains 15% salicin.

The pharmaceutically effective salts of glucosamine used in the invention are selected from the group consisting of glucosamine chloride, glucosamine bromide, glucosamine iodide and glucosamine sulfate. Similarly, with chondroitin the same type of salts are usable i.e., chondroitin chloride, chondroitin bromide, chondroitin sulfate and chondroitin iodide.

The *Angelica* root powder of the invention may be derived from *Angelica archangelica*, *Angelica sinensis*, *Angelica sylvestris*, *Angelica officinalis*, archangel, European angelica, garden Angelica, *Angelica acutiloba*, *Angelica pubescens*. *Angelica* root is preferred, but other parts of the plants can be used as well. *Angelica* contains a wide and complex variety of different constituents, of a defined and undefined nature. Preferred bioactive compounds are flavinoids, flavones and coumarins, preferably, osthole or 7-methoxy-8-(3-methylpent-2-enyl)coumarin, and alpha-angelicalactone. Other coumarins, include, e.g., meranzin hydrate, nodakentin, marmesinin, columbianadin, columbianetin, bergapten, heramandiol, 6-alkylcoumarins, angelol-type coumarins, byak-angelicin, ferulin, oxypeucedanin, umbelliprenin, imperatorin, neobyakangelicin, prenylcourmarins, glabralactone, anpubesol, angelical, angelin, furanocourmins, and derivatives thereof. Other bioactive agents include, e.g., linoleic acid, osthenol, falcarindiol, numerous flavinoids and flavones, 11(S), 16(R)-dihydroxyoctadeca-9Z, 17-diene-12,14-diyn-1-yl-acetate, xanthotoxin, umbelliferone, ferulic acid, magnesium, and derivatives thereof.

*Angelica* possesses a number of pharmacological activities, including, but not limited to smooth muscle relaxant activity, phosphodiesterase inhibition, calcium antagonist activity, cycloxygenase and 5-lipoxygenase inhibition, etc. Coumarins, and osthole in particular, have been identified to display activities such as, inhibition of platelet aggregation, inhibition of smooth muscle contraction, smooth muscle relaxation inhibition of calcium flux, cyclic nucleotide (such as cGMP and cAMP) phosphodiesterase inhibition, increase in cAMP and cGMP levels, anti-proliferative, anti-inflammatory, enhancement of the increase of cAMP and cGMP induced by forskolin, vasorelaxation, neurotransmitter receptor binding, such as GABA, 5HT-1A, D-2, and D-1 receptors. Alpha-angelicalactone also possesses various activities, including, e.g., calcium antagonism. Ferulic acid, another component of *Angelica* root also has been shown to scavenge oxygen free radicals and increase intracellular cAMP and cGMP. Preferred activities of *Angelica* are cyclic nucleotide phosphodiesterase inhibition, calcium antagonism, oxygen free radical scavenging, smooth muscle modulation, as either vasorelaxant or vasodilatory.

In making the compositions of the invention, the active materials will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methylcelluse, methyl and propylhydroxybenzoates, talc, magnesium stearate and mineral oil. The formulations can additionally include lubricating agents wetting agents, emulsifying and suspending agents, preserving agents, sweetening agents or flavoring agents. The compositions may be formulated so as to provide rapid, sustained or delayed release of the active ingredient after administration to the patient by employing procedures well-know in the art.

Further orally administrable compositions include hard capsules consisting of gelatine, and also soft, sealed capsules consisting of gelatine and a plasticizer, such as glycerol or sorbitol. The hard capsules may contain the active ingredients in the form of granules, for example in admixture with fillers, such as lactose, binders, such as starches, and/or glidants, such as talc or magnesium stearate, and where appropriate stabilizers. In soft capsules, the active ingredients are preferably dissolved or suspended in suitable liquids, such as fatty oils, paraffin oil, or liquid polyethylene glycols, and stabilizers may likewise be added. Amongst other forms, capsules, which can be both easily, chewed and also swallowed whole, are preferred.

The compositions of the invention can be prepared in a known manner, e.g. for example by means of conventional mixing, granulating, coating, dissolving or lyophilizing methods. Veterinary compositions for oral administration can be obtained, for example, by combining the active ingredients with solid carriers, granulating a resulting mixture where appropriate, and processing the mixture or granules, if desired or necessary, to form tablets or tablet cores following the addition of suitable excipients.

The active ingredients of the invention are used in these compositions in standardized solid form and preferably together with—at least—one of the adjuvants conventionally employed in the art of formulation, such as extenders, e.g. solvents or solid carriers, or surface-active compounds (surfactants). For usage in non-human animals, such as domestic animals, livestock, and pets of course only physiologically acceptable adjuvants are used.

One further embodiment of the present invention is a unique formulation that combines effective amounts of *Boswellia Serrata*, effective amounts of freeze dried green lipped mussle, effective amounts of white willow bark extract containing salicin, effective amounts of glucosamine and salts thereof, effective amounts of chondroitin and slats thereof and effective amounts of omega 3 fatty acids for direct oral administration.

In another preferred embodiment, a dosage for the composition for oral treatment of the present invention may consist of one or more capsules or tablets for mammal oral consumption. The dosage ranges defined herein before are meant per 1 Kg bodyweight per day. This dosage may be administered in a single daily dosage form in which all components are present. Alternatively, the nutritional supplement compositions for the present invention may be administered more than once, preferably twice, per day. The number of daily administrations will depend upon the needs of the mammal recipient. Different connective tissue disorders and injuries may require different amounts of the compositions of the present invention. In those regards, several dosages may be administered depending on the particular needs of the mammal.

This is the only product available which combines the above substances which are important for joint relief, cartilage metabolism and production of synovial fluid. Conditions in which embodiments of the present invention would be beneficial:

1) Osteoarthritis
2) Joint effusion
3) Joint inflammation and pain
4) Post operative arthroscopic surgery
5) Restoring proper joint function
6) Promote metabolic activity of chondrocytes (cartilage producing cells)
7) Inhibit enzymes that degrade cartilage
8) Stimulate the production of Hyaluronic acid.

The product of the invention provides clinical responses in about 3 to 10 days.

The present invention is illustrated by the following Examples, but should not be construed to be limited thereto. In the Examples, "part" and "%" are all part by weight or % by weight unless specified otherwise.

Example 1

| COMPONENTS | AMOUNT mg |
| --- | --- |
| Boswellia Serrata 65% | 167.50 |
| Biolane Green Lipped Mussel | 250.00 |
| White Willow Bark Extract 15% Salic | 200.00 |
| MEG 3 18/12 EPA/DHA Powder | 10.00 |
| Glucosamine Sulfate Potassium | 150.00 |
| Chondroitin Sulfate Sodium 85% | 55.00 |
| Silica-Sipernat | 1 |
| Magnesium stearate | 0.5 |

The above composition is filled into a hard gelatin capsule.

Example 2

| COMPONENTS | AMOUNT mg |
| --- | --- |
| Boswellia Serrata 65% | 177.50 |
| Biolane Green Lipped Mussel | 225.00 |

-continued

| COMPONENTS | AMOUNT mg |
|---|---|
| White Willow Bark Extract 15% Salic | 250.00 |
| MEG 3 18/12 EPA/DHA Powder | 15.00 |
| Glucosamine Sulfate Potassium | 175.00 |
| Chondroitin Sulfate Sodium 85% | 75.00 |
| Silica-Sipernat | 1 |
| Magnesium stearate | 0.5 |

The above composition is filled into a hard gelatin capsule.

Example 3

| COMPONENTS | AMOUNT mg |
|---|---|
| Boswellia Serrata 65% | 177.50 |
| Biolane Green Lipped Mussel | 225.00 |
| White Willow Bark Extract 15% Salic | 250.00 |
| MEG 3 18/12 EPA/DHA Powder | 15.00 |
| Glucosamine Sulfate Potassium | 175.00 |
| Chondroitin Sulfate Sodium 85% | 75.00 |
| Silica-Sipernat | 1 |
| Magnesium stearate | 0.5 |

The above composition is filled into a hard gelatin capsule.

Example 4

| COMPONENTS | AMOUNT mg |
|---|---|
| Boswellia Serrata 65% | 166.50 |
| Biolane Green Lipped Mussel | 175.00 |
| White Willow Bark Extract 15% Salic | 38.50 |
| MEG 3 18/12 EPA/DHA Powder | 50.00 |
| Glucosamine Sulfate Potassium | 50.00 |
| Angelica Root Extract 4:1 | 10.00 |
| Calcium Carbonate 36% granular | 4.0 |
| Sipernat-Silica | 1.0 |

The above composition is filled into a hard gelatin capsule.

Example 5

| COMPONENTS | AMOUNT mg |
|---|---|
| Boswellia Serrata 65% | 175.50 |
| Biolane Green Lipped Mussel | 200.00 |
| White Willow Bark Extract 15% Salic | 45.50 |
| MEG 3 18/12 EPA/DHA Powder | 75.00 |
| Glucosamine Sulfate Potassium | 65.00 |
| Angelica Root Extract 4:1 | 12.00 |
| Calcium Carbonate 36% granular | 4.0 |
| Sipernat-Silica | 1.0 |

The above composition is filled into a hard gelatin capsule.

Example 6

| COMPONENTS | AMOUNT mg |
|---|---|
| Boswellia Serrata 65% | 175.50 |
| Angelica Root Extract 4:1 | 12.00 |
| Calcium Carbonate 36% granular | 4.0 |
| Sipernat-Silica | 1.0 |

The above composition is filled into a hard gelatin capsule.

Example 7

Study of Anti-Inflammatory Activity in a Model of Formalin-Induced Arthritis in Rats The model of arthritis in animals is caused by injection of 0.1 ml of 2% formalin solution into the cavity of the knee joint. After 24 hrs a model of acute arthritis is obtained, which is suitable for studying the anti-inflammatory and anaesthetizing action of the preparations. Butadion and diclofenac are used as control preparations. The present agent (3 doses of Example 6) are dissolved in corn oil and administered according to the following regimen: 3 days prior to inflammation one time per day intraperitoneally (by a probe) and on the 4th day 4 hours prior to the injection of formalin. The treatment is conducted over a period of 7 days by administering the investigated preparation one time per day. The evaluation of the results of treatment is conducted on the 4th and 8th day. Anti-inflammatory activity was estimated using the parameters of volume, pain sensitivity and inflammation temperature of the extremity. The total activity index is calculated (total percentages of decrease in size of the affected extremity for 7 days) and the therapeutic index (ratio of the total activity index of the preparation to the total activity index of the group with formalin).

With respect to the anaesthetizing and febrifugal activity the present agent exceeded the effect of butadion at all doses and it is practically not inferior to the effect of diclofenac at a dose of 250 mg/kg.

In the model of formalin arthritis, the talocrural joints of rats and gastric mucosa are also investigated. Histological sections included the zone of the joint with adjacent parts of bone tissue, surrounding soft tissues which are intimately connected to the joint including the adjacent derma, and in a series of observations also epidermis.

During the macroscopic inspection of the joints of the control group rats (formalin-induced arthritis without treatment) an enlargement of the joint and smoothening of its outlines is observed. At the incision periarticular tissues is edematic. A small quantity of unclear liquid occurs in the cavity of the joint. And the articulate surfaces of the cartilages are smooth. During the microscopic examination of the knee joint plethora and edema of periarticular tissues are observed, as well as changes in the synovial membrane, in the fibers of which the plethora, edema and lymphoid infiltration of areolar tissue of fibres are noted.

The joints of rats treated with the present agent do not show any pronounced macroscopic changes. Histologically, the synovial membrane, which lines the surface of the joint, consisted of less differentiated cells of connective tissue with round or oval nuclei. Plethoras or lymphoid infiltrations are not observed.

During the dissection of the experimental rats, the size and the shape of stomach and intestine did not show changes. The mucous membrane of the stomach body is bright, smooth and light pink. The lumen of the small intestine over the whole length was uniform. The mucous membrane of the small intestine is bright, smooth and light pink.

During the histological study of stomach and small intestine no destructive or inflammatory changes in the mucous membranes is noted. The epithelium of the mucous membrane of the small intestine do not show changes either.

All patents, patent applications and publications cited in this application including all cited references in those patents, applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting.

It is to be understood that the terms used herein are merely descriptive rather than limiting and that various changes, numerous equivalents may be made without departing from the spirit or scope of the claimed invention.

What we claim is:

1. A tablet or capsule for the treatment of arthritis, joint stiffness, joint mobility and joint pain in vertebrates, consisting essentially of therapeutically effective amounts of Angelica root extract, green lipped mussel extract, glucosamine and chondroitin.

* * * * *